United States Patent [19]

Bitha et al.

[11] Patent Number: 4,992,449
[45] Date of Patent: Feb. 12, 1991

[54] 7-(SUBSTITUTED)CYCLOALKYLAMINO-1-(SUBSTITUTED)-6-FLUORO-1,4-DIHYDRO-4-OXO-3-QUINOLINECARBOXYLIC ACIDS

[75] Inventors: Panayota Bitha, Nanuet; Yang-I Lin, Tappan, both of N.Y.

[73] Assignee: American Cyanamid Company, Stamford, Conn.

[21] Appl. No.: 473,498

[22] Filed: Feb. 1, 1990

[51] Int. Cl.$^5$ .................. A61K 31/47; C07D 215/333
[52] U.S. Cl. ..................................... 514/312; 546/156
[58] Field of Search ...................... 546/156; 514/312

[56] References Cited

U.S. PATENT DOCUMENTS

| | | | |
|---|---|---|---|
| 3,960,868 | 6/1976 | Ferrini et al. | 546/156 |
| 4,588,726 | 5/1986 | Petersen | 514/254 |
| 4,617,308 | 10/1986 | Mich | 514/312 |
| 4,657,913 | 4/1987 | Mich | 514/278 |
| 4,666,920 | 5/1987 | Grohe | 514/312 |
| 4,668,680 | 5/1987 | Trehan | 514/254 |
| 4,692,454 | 9/1987 | Mich | 514/312 |
| 4,698,350 | 10/1987 | Daum | 514/312 |
| 4,703,047 | 10/1987 | Petersen | 514/254 |
| 4,753,925 | 6/1988 | Grohe | 514/254 |
| 4,775,668 | 10/1988 | Jefson | 514/183 |
| 4,801,584 | 1/1989 | Yokose | 514/183 |
| 4,806,539 | 2/1989 | Petersen | 514/254 |
| 4,816,451 | 3/1989 | Schriewer | 514/185 |
| 4,851,415 | 7/1989 | Mich | 514/278 |
| 4,864,023 | 9/1989 | Yokose | 514/66 |
| 4,880,814 | 11/1989 | Chu et al. | 546/156 |

OTHER PUBLICATIONS

Rosen, J. Med. Chem., 1988, 31, 1598–1611.
Wentland, J. Med. Chem., 1988, 31, 1694–1697.
Domagala, J. Med. Chem., 1986, 29, 394–404.
Sanchez, J. Med. Chem., 1988, 31 983–991.
Domagala, J. Med. Chem., 1988, 31, 991–1001.
Wentland, J. Med. Chem., 1984, 27, 1103–1108.
Abstract for EP350733 (1/17/90).
Abstract for EP326916 (8/9/89).
Abstract for EP 321191 (6/21/89).
Abstract for JP 100165 (4/18/89).
Abstract for EP 305744 (3/8/89).
Abstract for EP297858 (1/4/89).
Abstract for EP 251308 (1/7/88).
Abstract for EP230053 (7/29/87).
Ziegler et al., J. Het. Chem., 26, p. 1141 (1989).

*Primary Examiner*—Mukund J. Shah
*Assistant Examiner*—E. Bernhardt
*Attorney, Agent, or Firm*—Thomas S. Szatkowski

[57] ABSTRACT

Novel antibacterial compounds of the formula:

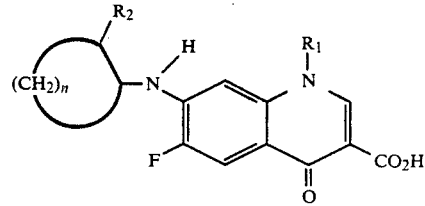

in which $R_1$ is alkyl ($C_1$–$C_4$), cycloalkyl ($C_3$–$C_6$), alkoxy ($C_1$–$C_4$), alkylamino ($C_1$–$C_3$), vinyl, phenyl, benzyl, —$CH_2CH_2F$ or mono or polysubstituted phenyl (wherein the substituent is halogen, $CF_3$ or $OCH_2F$); n is an integer of from 1 to 4; and $R_2$ is cis or trans hydroxy, amino, mono or disubstituted alkyl ($C_1$–$C_3$) amino and the pharmacologically accepted salts thereof are described.

13 Claims, No Drawings

7-(SUBSTITUTED)CYCLOALKYLAMINO-1-(SUBSTITUTED)-6-FLUORO-1,4-DIHYDRO-4-OXO-3-QUINOLINECARBOXYLIC ACIDS

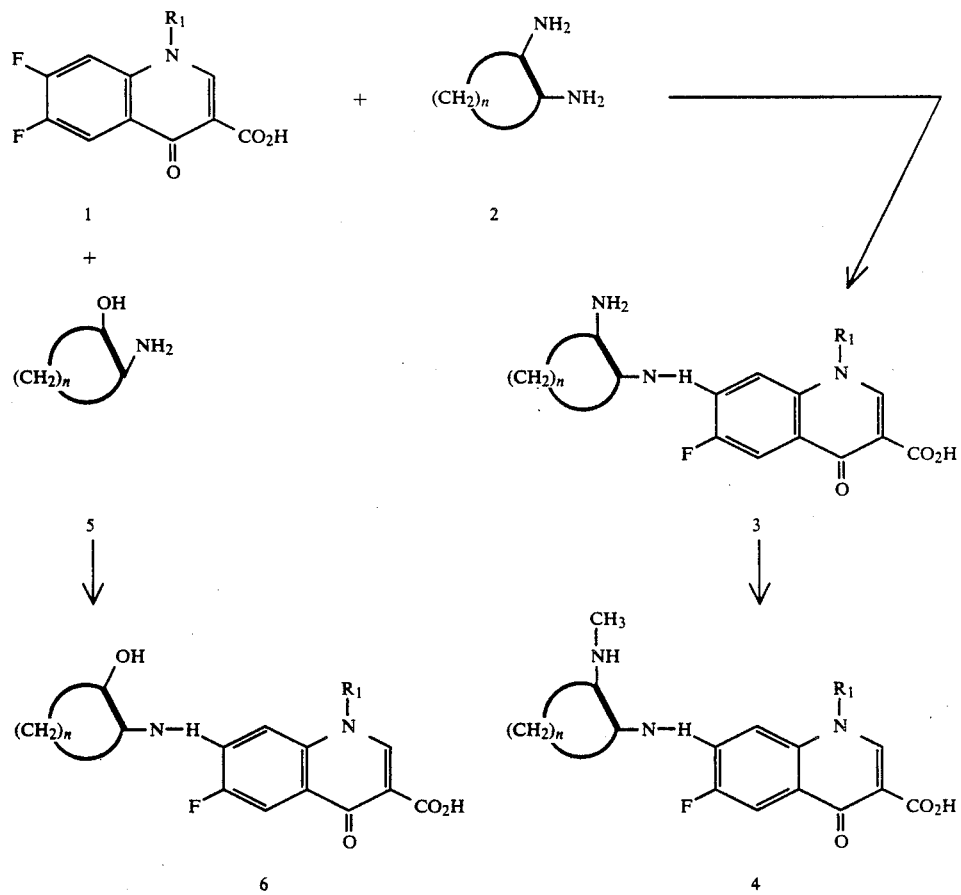

BACKGROUND OF THE INVENTION

The invention relates to 7-(substituted) cycloamino -1-(substituted)-6-fluoro-1,4-dihydro-4-oxo-3-quinolinecarboxylic acids and their salts as antibacterial agents and a method of preparation.

SUMMARY OF THE INVENTION

The invention provides to the art new compounds of the Formula I:

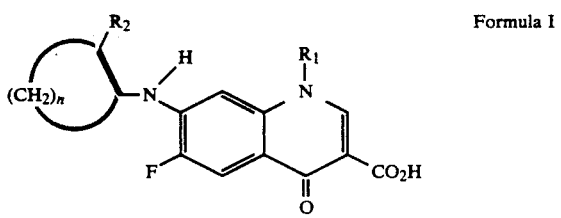

Formula I wherein $R_1$ is alkyl ($C_3$–$C_4$), cycloalkyl ($C_3$–$C_6$), alkoxy ($C_1$–$C_4$), alkylamino ($C_1$–$C_3$), vinyl, phenyl, benzyl, —$CH_2CH_2F$ or mono or polysubstituted phenyl (wherein the substituent is halogen, $CF_3$ or $OCH_2F$); n is an integer of from 1 to 4; and $R_2$ is cis or trans hydroxy, amino, mono or disubstituted alkyl ($C_1$–$C_3$) amino and the pharmacologically accepted salts thereof.

The compounds of the present invention may be prepared according to the following reaction scheme:

According to the above scheme, a 1-(substituted)-6,7-difluoro-1,4-dihydro-4-oxo-3-quinolinecarboxylic acid 1 with $R_1$ defined above is reacted with a cis or trans 1,2-diaminocycloalkane 2, with n defined above, in pyridine at 100°–120° C. from one to three hours giving the 7-(2-aminocycloalkylamino)-1-(substituted)-6-fluoro -1,4-dihydro-4-oxo-3-quinolinecarboxylic acid 3. Suitable 1,2 diaminocycloalkanes include cis and trans cyclopropanediamine; cis and trans 1,2 diaminocyclobutane; cis and trans 1,2 cyclopentanediamine; and cis and trans 1,2 diaminocyclohexane. Reaction of 3 with formation and formic acid at 110° C. for two hours gives substituted product 4.

Reaction of a 1-(substituted)-6,7-difluoro1,4-dihydro-4-oxo-3-quinolinecarboxylic acid 1, with a cis or trans 1,2-aminocyclohexanol 5, with n defined above, in pyridine at 100°–120° C. from one to three hours gives compound 6.

The following are illustrations of the 2-substituted cycloalkylamino substituents for the "seven" (7) position of the above quinolinecarboxylic acid compounds of the present invention, with $R_2$ defined above:

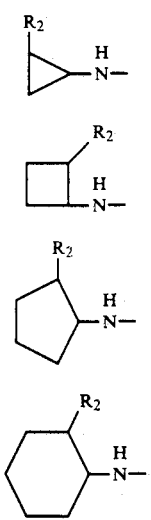

The compounds of the present invention are active antibacterial agents as established in the following in vitro test. As such, they are effective in treating bacterial infections in warm-blooded animals.

The in vitro antimicrobial spectrum of the compounds of this invention were determined by the agar plate dilution method with Mueller-Hinton agar and an inoculum of each test organism of approximately $10^4$ colony forming units delivered by the Steers replicating device. The minimal inhibitory concentration (MIC) in mcg/ml is defined as the lowest concentration of test compound that inhibited visible growth after 18 hours incubation at 35° C. Results are given in Table I, with the test compounds identified by the number of their hereinafter described examples

TABLE I

| | In vitro Antibacterial Spectrum | | | |
|---|---|---|---|---|
| | Compounds Listed by Example No. MIC (mcg/ml) | | | |
| Organism and No. | 1 | 2 | 3 | 4 |
| Escherichia coli MOR 84-20 | 0.25 | 0.50 | 2.00 | 1.00 |
| Escherichia coli VGH 84-19 | 0.25 | 1.00 | 2.00 | 1.00 |
| Escherichia coli CMC 84-50 | 1.00 | 0.50 | 4.00 | 2.00 |

TABLE I-continued

| | In vitro Antibacterial Spectrum | | | |
|---|---|---|---|---|
| | Compounds Listed by Example No. MIC (mcg/ml) | | | |
| Organism and No. | 1 | 2 | 3 | 4 |
| Klebsiella neumoniae CMC 84-31 | 1.00 | 2.0 | 4.00 | 2.00 |
| Klebsiella neumoniae MOR 84-24 | 1.00 | 1.00 | 4.00 | 2.00 |
| Klebsiella neumoniae IO 83-5 | 1.00 | 2.00 | 4.00 | 2.00 |
| Enterobacter cloacae VGH 84-39 | 0.500 | 1.0 | 2.00 | 1.00 |
| Enterobacter cloacae K 84-10 | 0.500 | 1.00 | 2.00 | 1.00 |
| Enterobacter cloacae MOR 84-30 | 1.00 | 2.00 | 8.00 | 4.00 |
| Serratia marcescens MOR 84-41 | 0.500 | 1.00 | 4.00 | 1.00 |
| Serratia marcescens CMC 83-74 | 16.00 | >16.00 | >16.00 | >16.00 |
| Serratia marcescens IO 83-63 | 1.00 | 2.00 | 4.00 | 1.00 |
| Moranella morganii VGH 84-12 | 1.00 | 4.00 | 4.00 | 2.00 |
| Moranella morganii CMC 84-38 | 1.00 | 1.00 | 8.00 | 1.00 |
| Morganella morganii MOR 84-45 | 0.50 | 2.00 | 4.00 | 0.50 |
| Proteus rettgeri IO 83-21 | 2.00 | 4.00 | 4.00 | 2.00 |
| Providencia stuartii CMC 83-3 | >16.00 | >16.00 | >16.00 | >16.00 |
| Citrobacter diversus K 82-24 | 0.25 | 0.50 | 2.00 | 0.50 |
| Pseudomonas aeruginosa VGH 84-16 | 8.0 | 16.00 | >16.00 | >16.00 |
| Pseudomonas aeruginosa VGH 84-3 | >16.0 | >16.0 | >16.0 | >16.0 |
| Pseudomonas aeruginosa CMC 83-20 | 4.00 | 8.00 | >16.00 | >16.00 |
| Staphylococcus aureus VGH 84-47 | 2.00 | 4.00 | 4.00 | 2.00 |
| Staphylococcus aureus K 82-26 | 2.00 | 4.00 | 4.00 | 1.00 |
| Staphylococcus aureus CMC 83-131 | 4.00 | >16.00 | >16.00 | NT |
| Streptococcus faecalis UCI 85-30 | 4.00 | >16.00 | >16.00 | 4.00 |
| Staphylococcus faecalis VGH 84-69 | 4.00 | >16.00 | >16.00 | 4.00 |
| Staphylococcus faecalis CMC 83-120 | 4.00 | >16.00 | >16.00 | 4.00 |
| Escherichia coli ATCC 25922 | 0.25 | 0.50 | 2.00 | 0.50 |
| Staphylococcus aureus ATCC 29213 | 2.00 | 4.00 | 4.00 | 4.00 |

TABLE II

| | In vitro Antibacterial Spectrum | | | | | | | |
|---|---|---|---|---|---|---|---|---|
| | Compounds Listed by Example No. MIC (mcg/ml) | | | | | | | |
| Organism and No. | 3 | 4 | 5 | 6 | 7 | 8 | 9 | 10 |
| Excherichia coli ATCC 25922 | 1.00 | 2.00 | 32.00 | 0.50 | 32.00 | 32.00 | 32.00 | 8.00 |
| Excherichia coli LL 311 | 1.00 | 2.00 | 16.00 | 0.50 | 32.00 | 32.00 | 32.00 | 4.00 |
| Excherichia coli CMC 84-11 | 1.00 | 2.00 | 32.00 | 0.50 | 16.00 | 16.00 | 16.00 | 4.00 |
| Serratia marcescens K 84-18 | 2.00 | 4.00 | 64.00 | 1.00 | 64.00 | 32.00 | 32.00 | 8.00 |
| Serratia marcescens VGH 84-30 | 8.00 | 16.00 | >128.00 | 4.00 | 128.00 | 128.00 | 128.00 | 32.00 |
| Proteus rettgeri CMC 84-41 | 4.00 | 8.00 | 64.00 | 1.00 | 128.00 | 128.00 | 128.00 | 32.00 |
| Morganella morganii CMC 84-37 | 4.00 | 4.00 | 32.00 | 0.50 | 32.00 | 32.00 | 32.00 | 8.00 |
| Pseudomonas aeruginosa LL-1244 | 16.00 | 32.00 | >128.00 | 8.00 | 128.00 | >128.00 | 128.00 | 128.00 |
| Pseudomonas aeruginosa VGH 84-4 | 16.00 | 64.00 | >128.00 | 8.00 | 128.00 | >128.00 | 128.00 | 128.00 |
| Staphylococcus aureus VGH 84-45 | 4.00 | 64.00 | 32.00 | 2.00 | 128.00 | 128.00 | 128.00 | 4.00 |
| Staphylococcus aureus Smith 1 | 2.00 | 8.00 | 8.00 | 0.50 | 16.00 | 16.00 | 128.00 | 2.00 |
| Streptococcus faecalis VGH 84-65 | 64.00 | 32.00 | >128.00 | 8.00 | 64.00 | 64.00 | 64.00 | 32.00 |
| Streptococcus faecalis UCI 85-19 | 64.00 | 32.00 | >128.00 | 8.00 | 128.00 | 128.00 | 128.00 | 32.00 |
| Staphylococcus aureus ATCC 29213 | 4.00 | 128 | 64.00 | 8.00 | >128.00 | 128.00 | >128.00 | 8.00 |
| Staphylococcus SSC 82-56 | 2.00 | NT | NT | NT | NT | NT | NT | NT |

TABLE II-continued

| | In vitro Antibacterial Spectrum | | | | | | | |
|---|---|---|---|---|---|---|---|---|
| | Compounds Listed by Example No. MIC (mcg/ml) | | | | | | | |
| Organism and No. | 3 | 4 | 5 | 6 | 7 | 8 | 9 | 10 |
| *Staphylococcus aureus* NEMC 87-59 | 4.00 | NT | NT | NT | NT | NT | NT | NT |

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day, or in sustained release form. For most large mammals the total daily dosage is from about 100 to about 750 mg, preferably from about 100 to 500 mg. Dosage forms suitable for internal use comprise from about 100 to 750 mg of the active compound in intimate admixture with a solid or liquid pharmaceutically acceptable carrier. This dosage regimen may be adjusted to provide the optimal therapeutic response For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

Cis-7-[(2-Aminocyclohexyl)amino]1-cyclopropyl-6-fluoro-1,4-dihydro-4-oxo-3-quinolinecarboxylic acid A mixture of 1.33 g of 1-cyclopropyl-6,7-difluoro-1,4-dihydro-4-oxo-3-quinolinecarboxylic acid and 1.73 g of cis-1,2-diaminocyclohexane in 10 ml of pyridine was heated in an oil bath of 115° C. for 1 hour then filtered while hot. Cooling the filtrate afforded 1.09 g of the desired product, m.p. 270°-274° C.

EXAMPLE 2

Cis-7-[(2-Aminocyclopentyl)amino]-1-cyclopropyl-6-fluoro-1,4-dihydro-4-oxo-3-quinolinecarboxylic acid A mixture of 663 mg of l-cyclopropyl-6 7-difluoro-1,4-dihydro-4-oxo-3-quinolinecarboxylic acid and 1.0 g of cis-1,2-cyclopentanediamine in 2.5 ml of pyridine was reacted as described in Example 1 giving 713 mg of the desired product, m.p. 240° C. dec.

EXAMPLE 3

Cis-7-[2-Aminocyclopentyl)amino]-6-fluoro-1-(4-fluoro phenyl)-1-4-dihydro-4-oxo-3-quinolinecarboxylic acid The procedure of Example 1 was followed using 38 mg of 6,7-difluoro-1-(4-fluorophenyl)-1,4-dihydro-4-oxo-3-quinolinecarboxylic acid and 601 mg of cis-1,2-cyclopentanediamine in 2 ml of pyridine giving 595 mg of the desired product, m.p. 237° C. dec.

EXAMPLE 4

Cis-7-[(2-Aminocyclopentyl)amino]-1-ethyl-6-fluoro-1,4-dihydro-4-oxo-3-quinolinecarboxylic acid The procedure of Example 1 was followed using 0.6 g of 1-ethyl-6,7-difluoro-1,4-dihydro-4-oxo-3-quinolinecarboxylic acid and 1.0 g of cis-1,2-cyclopentanediamine in 4 ml of pyridine, giving 0.5 g of the desired product, m.p. 233°-235° C.

EXAMPLE 5

Cis-7-[(2-Hydroxycyclohecxyl)amino]-1-ethyl-6-fluoro-1,4-dihydro-4-oxo-3-quinolinecarboxylic acid A mixture of 1.27 g of 1-ethyl-6,7-difluoro-1,4-dihydro-4-oxo-3-quinolinecarboxylic acid and 3.79 g of cis-2-aminocyclohexanol, made from the hydrochloride salt by extraction from aqueous sodium hydroxide with ether, in 7 ml of pyridine was further reacted as described in Example 1, giving 1.25 g of the desired product, m.p. 257°-259° C.

EXAMPLE 6

Cis-7-[(2-Aminocyclohexyl)amino]-1-ethyl-6-fluoro-1,4-dihydro-4-oxo-3-quinolinecarboxylic acid A mixture of 2.53 g of 1-ethyl-6,7-difluoro-1,4-dihydro-4-oxo-3-quinolinecarboxylic acid and 4.6 g of cis-1,2-diaminocyclohexane in 10 ml of pyridine was heated as described in Example 1 giving 2.4 g of the desired product, m.p. 225°-227°C.

EXAMPLE 7

Trans-(+/−)-7-[(2-Aminocyclohexyl)amino]1-ethyl-6-fluoro-1,4-dihydro-4-oxo-3-quinolinecarboxylic acid A mixture of 2.53 g of 1-ethyl-6,7-difluoro-1,4-dihydro-4-oxo-3-quinolinecarboxylic acid and trans-dl-1,2-diaminocyclohexane in 10 ml of pyridine was reacted as described in Example 1 giving 3.0 g of the desired product, m.p. 216°-217° C.

EXAMPLE 8

Trans-(−)-7-[(2-Aminocyclohexyl)amino]-1-ethyl-6-fluoro-1,4-dihydro-4-oxo-3-quinolinecarboxylic acid A mixture of 2.53 g of 1-ethyl-6 7-difluoro-1,4- dihydro-4-oxo-3-quinolinecarboxylic acid and 4.6 g of trans-(−)-1,2-diaminocyclohexane in 10 ml of pyridine was reacted as described in Example 1 to give 2.3 g of the desired product, m.p. 230°-231°C.

EXAMPLE 9

Trans-(+)-7-[(2-Aminocyclohexyl)amino]-1-ethyl-6-fluoro-1,4-dihydro-4-oxo-3-quinolinecarboxylic acid A mixture of 2.53 g of 1-ethyl-6,7-difluoro-1,4-dihydro-4-oxo-3-quinolinecarboxylic acid and 4.6 g of trans(+)-S,S-1,2-diaminocyclohexane in 10 ml of pyridine was reacted as described in Example 1 to give 2.8 g of the desired product, m.p. 230° dec.

EXAMPLE 10

Cis-7-[(2-Methylamino)cyclohexyl]amino]-1-ethyl-6-fluoro-1,4-dihydro-4-oxo-3-quinolinccarboxylic acid A mixture of 300 mg of cis-7-[(2-aminocyclohexyl)amino]-1-ethyl-6-fluoro-1,4-dihydro-4-oxo-3-quinolinecarboxylic acid, 3.6 ml of 37% formaldehyde and 4.5 ml of 90% formic acid was heated at 110° C. for 2 hours. The volatiles were removed and 10 ml of water added to the residue. The pH was adjusted to 7.0 with 1N sodium hydroxide. The solid was collected, washed with water and dried to give 0.23 g of the desired product.

EXAMPLE 11 cis-7-[(2-aminocyclopropyl)amino]-1-ethyl-6-fluoro-1,4-dihydro-4-oxo-3-quinoline carboxylic acid A mixture of 1-ethyl-6,7-difluoro-1,4-dihydro-4-oxo-3-quinoline carboxylic acid and cis 1,2-diamino cyclopropane [Synthetic Communications, 11(6), 493-495 (1981)] in pyridine is reacted as described in Example 1 giving the desired product.

EXAMPLE 12

7-[(2-aminocyclobutyl)amino]-1-ethyl-6-fluoro-1,4-dihydro-4-oxo-3 quinoline carboxylic acid A mixture of 1-ethyl-6,7-difluoro-1,4-dihydro-4-oxo-3-quinoline carboxylic acid and 1,2 diaminocyclobutane [The American Chemical Society, Vol. 64, p. 2696 (1942)] in pyridine is reacted as described in Example 1 giving the desired product.

We claim:

1. A compound of the formula:

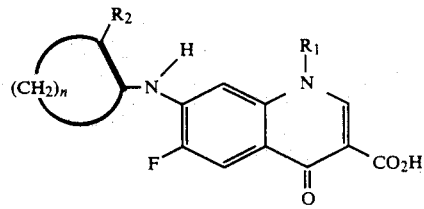

wherein $R_1$ is alkyl ($C_1$-$C_4$), cycloalkyl ($C_3$-$C_6$), alkoxy ($C_1$-$C_4$), alkylamino ($C_1$-$C_3$), vinyl, phenyl, benzyl, —$CH_2CH_2F$ or mono or polysubstituted phenyl (wherein the substituent is halogen, $CF_3$, or $OCH_2F$); n is an integer of from 1 to 4 and; $R_2$ is cis or trans hydroxy, amino, mono or disubstituted alkyl ($C_1$-$C_2$) amino and the pharmacologically accepted salts thereof.

2. The compound according to claim 1, cis-7-[(2-aminocyclohexyl)amino]-1-cyclopropyl-6-fluoro-1,4-dihydro-4-oxo-3-quinolinecarboxylic acid.

3. The compound according to claim 1, cis-7-[(2-aminocyclopentyl)amino]-1-cyclopropyl-6- fluoro-1,4-dihydro-4-oxo-3-quinolinecarboxylic acid.

4. The compound according to claim 1, cis-7-[(2-aminocyclopentyl)amino]-6-fluoro-1-(4- fluorophenyl)-1,4-dihydro-4-oxo-3-quinolinecarboxylic acid.

5. The compound according to claim 1, cis-7-[(2-aminocyclopentyl)amino]-1-ethyl-6-fluoro-1,4-dihydro-4-oxo-3-quinolinecarboxylic acid.

6. The compound according to claim 1, cis-7-[(2-hydroxycyclohexyl)amino]-1-ethyl-6-fluoro-1,4-dihydro-4-oxo-3-quinolinecarboxylic acid.

7. The compound according to claim 1, cis-7-[(2-aminocyclohexyl)amino]-1-ethyl-6-fluoro-1, 4-dihydro-4-oxo-3-quinolinecarboxylic acid.

8. The compound according to claim 1, trans-(+/−)-7-[(2-aminocyclohexyl)amino]-1-ethyl-6-fluoro-1,4-dihydro-4-oxo-3-quinolinecarboxylic acid.

9. The compound according to claim 1, trans-(−)-7-[(2-aminocyclohexyl)amino]-1-ethyl-6-fluoro-1,4-dihydro-4-oxo-3-quinolinecarboxylic acid.

10. The compound according to claim 1, trans-(+)-7-[(2-aminocyclohexyl)amino]-1-ethyl-6-fluoro-1,4-dihydro-4-oxo-3-quinolinecarboxylic acid.

11. The compound according to claim 1, cis-7-[(2-methylamino)cyclohexyl]amino]-1-ethyl-6-fluoro-1,4-dihydro-4-oxo-3-quinolinecarboxylic acid.

12. A method of treating bacterial infections in warm-blooded animals which comprises administering to said animals, an antibacterially effective amount of a compound selected from those in claim 1.

13. An antibacterial composition of matter in unit dosage form comprising from 100 to 750 mg of a compound selected from those of claim 1, in association with a pharmaceutically acceptable carrier.

* * * * *